(12) United States Patent
Sakhel

(10) Patent No.: US 8,573,221 B2
(45) Date of Patent: Nov. 5, 2013

(54) CERVICAL OCCLUDER

(75) Inventor: Khaled Sakhel, Virginia Beach, VA (US)

(73) Assignee: Eastern Virginia Medical School, Norfolk, VA (US)

( * ) Notice: Subject to any disclaimer, the term of this patent is extended or adjusted under 35 U.S.C. 154(b) by 841 days.

(21) Appl. No.: 12/572,705

(22) Filed: Oct. 2, 2009

(65) Prior Publication Data

US 2011/0079226 A1 Apr. 7, 2011

(51) Int. Cl.
*A61F 6/06* (2006.01)

(52) U.S. Cl.
USPC .......................... 128/830; 128/834

(58) Field of Classification Search
USPC .......... 128/830–841; 606/139–141, 144, 151, 606/157
See application file for complete search history.

(56) References Cited

U.S. PATENT DOCUMENTS

| | | |
|---|---|---|
| 5,059,198 A | 10/1991 | Gimpelson |
| 5,217,466 A | 6/1993 | Hasson |
| 5,368,598 A | 11/1994 | Hasson |
| 5,395,354 A | 3/1995 | Vancaillie |
| 5,509,893 A | 4/1996 | Pracas |
| 5,540,658 A | 7/1996 | Evans et al. |
| 5,562,680 A | 10/1996 | Hasson |
| 5,865,729 A | 2/1999 | Meehan et al. |
| 6,024,696 A | 2/2000 | Hoftman et al. |
| 6,280,379 B1 | 8/2001 | Resnick |
| 6,346,102 B1 | 2/2002 | Harrington et al. |
| 6,712,761 B2 | 3/2004 | Borodulin et al. |
| 6,761,687 B1 | 7/2004 | Doshi et al. |
| 6,905,472 B2 * | 6/2005 | Welch ........................ 600/591 |
| 6,960,166 B1 | 11/2005 | Wong et al. |
| 7,070,561 B1 | 7/2006 | Ansari |
| 7,479,145 B2 | 1/2009 | Burbank et al. |
| 2006/0173468 A1 | 8/2006 | Simmon et al. |
| 2008/0243183 A1 * | 10/2008 | Miller et al. ................ 606/228 |
| 2008/0306334 A1 * | 12/2008 | Okada ........................ 600/104 |

OTHER PUBLICATIONS

PCT/US10/51308 International Search Report (mailed Dec. 1, 2010) (2 pages).

* cited by examiner

*Primary Examiner* — Patricia Bianco
*Assistant Examiner* — Keri J Nelson
(74) *Attorney, Agent, or Firm* — Wilmer Cutler Pickering Hale and Dorr LLP

(57) ABSTRACT

A device for occluding a cervix has an elongated conduit sized and shaped to extend from a proximal end outside the vagina to a distal end near the cervix. A loop sized to fit around an exocervix is provided at the distal end. The loop is sufficiently flexible to be tightened and loosened around the exocervix. The device has a rod inside the conduit. The rod has a distal end and a proximal end, and the loop is joined to the distal end of the rod. Moving the rod longitudinally relative to the conduit tightens or loosens the loop.

19 Claims, 3 Drawing Sheets

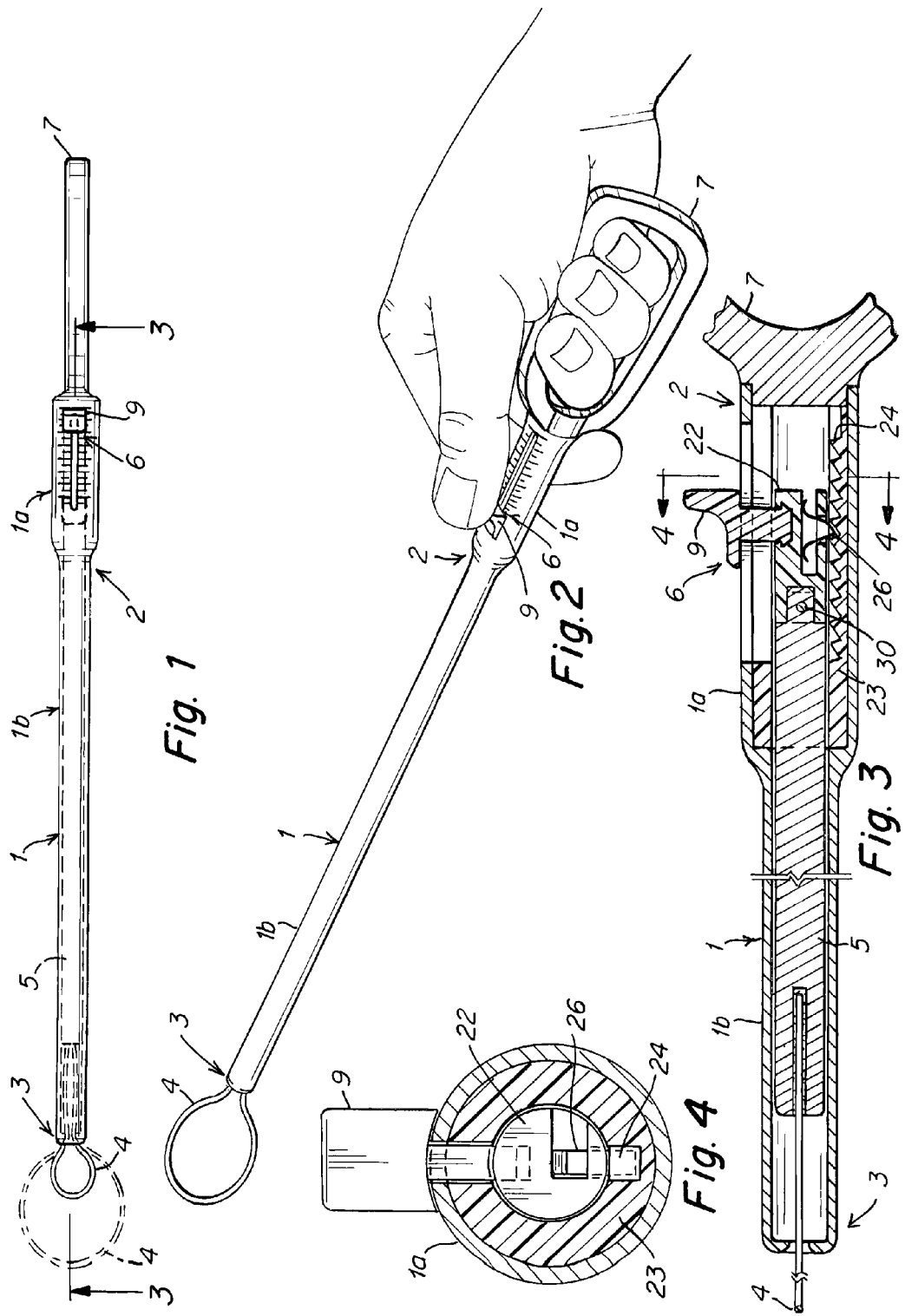

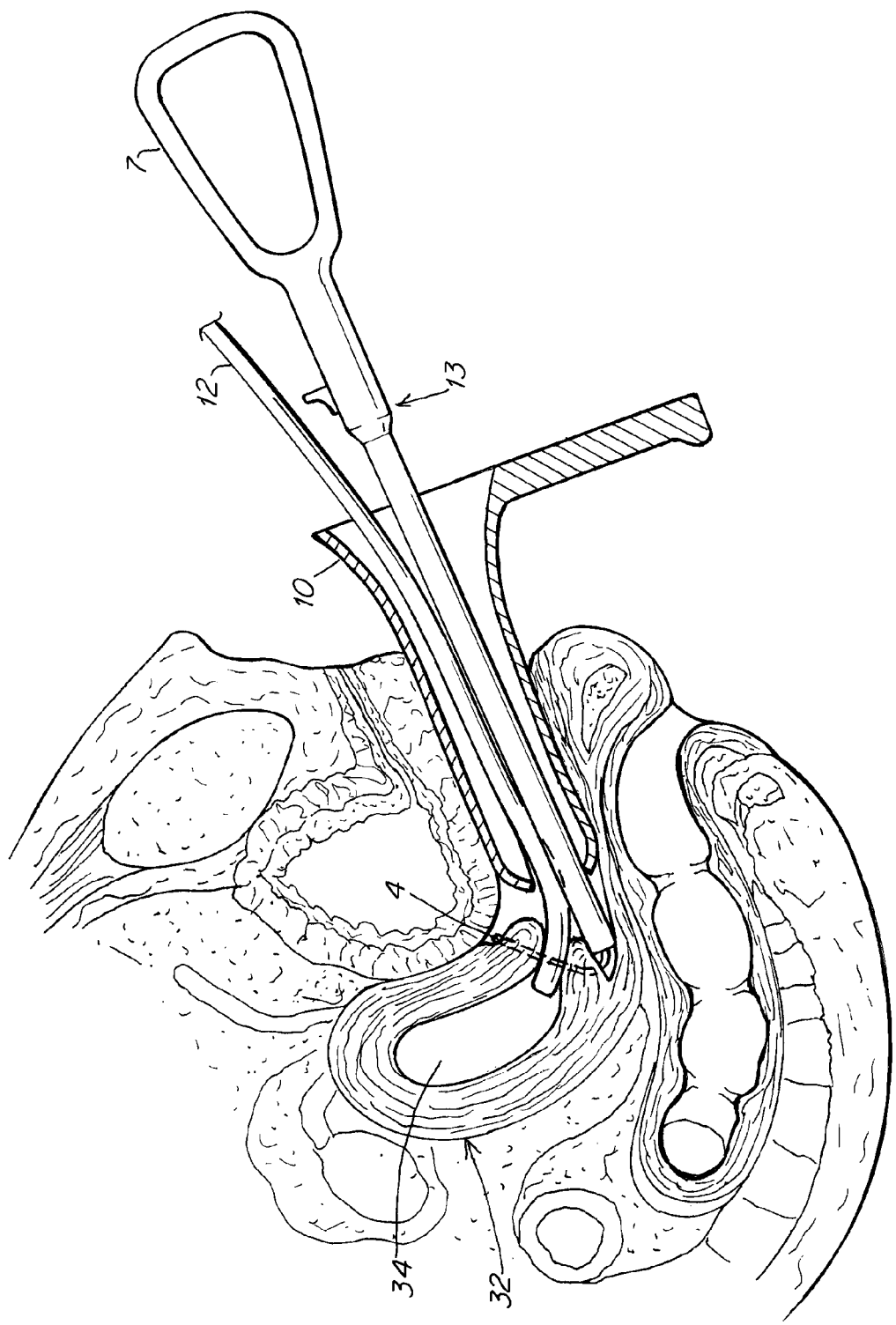

CERVICAL OCCLUDER

FIELD

This disclosure relates generally to a device for occluding a cervix.

BACKGROUND

During certain gynecological procedures, the uterine cavity might need to be distended, such as by injecting a gas or a liquid into the uterus. These procedures include hysteroscopic procedures and saline infusion sonography such as the diagnosis and treatment of uterine conditions including, but not limited to, endometrial polyps, abnormal uterine bleeding, uterine fibroids, uterine malformations, sterilization, and infertility work-up. During such distention, if the cervix is not occluded or some other action is not taken, the gas or liquid could escape through the cervix and allow the uterus to contract back to its normal size.

Currently, during procedures where the cervix must be occluded, practitioners can use tenaculums or similar devices to occlude the cervix. However, tenaculums grip and pierce the tissue of the cervix, and this can cause pain and discomfort to the patient.

SUMMARY

This disclosure describes a device for occluding a cervix inside a vagina. In one aspect, the device has an elongated conduit sized and shaped to extend from a proximal end outside the vagina to a distal end near the cervix. The device also comprises a loop sized to fit around an exocervix. The loop is sufficiently flexible to be tightened and loosened around the exocervix. A portion of the loop is disposed inside the conduit, and a portion of the loop protrudes from the distal end of the conduit.

The device includes a rod inside the conduit and movable relative to the conduit. The rod has a distal end and a proximal end, and the loop is joined to the distal end of the rod. Moving the rod longitudinally relative to the conduit tightens or loosens the loop.

This disclosure also includes a method for occluding a cervix. In this method, a device is inserted into a patient's vagina. The device has an elongated conduit sized and shaped to extend from a proximal end outside the vagina to a distal end near the cervix. The device also comprises a loop sized to fit around an exocervix. The loop is sufficiently flexible to be tightened and loosened around the exocervix. A portion of the loop is disposed inside the conduit and a portion of the loop protrudes from the distal end of the conduit, allowing the loop to be tightened to a closed position and loosened to an open position. The device additionally comprises a rod disposed inside the conduit and coupled to the loop to allow the practitioner to tighten or loosen the loop around the patient's exocervix.

The cervical occluding device permits a practitioner to occlude the cervix during gynecological procedures. After the cervix is occluded, the uterus can be distended with a fluid. Then, procedures can be implemented, such as treating endometrial polyps, abnormal uterine bleeding, uterine fibroids, uterine malformations, sterilization, and infertility work-up. The device also can reduce the amount of injury and discomfort a patient experiences and allows for a more flexible environment for a clinician to work in.

BRIEF DESCRIPTION OF THE FIGURES

FIG. 1 is a side view of an embodiment of a cervical occluding device.

FIG. 2 is a view of the cervical occluding device of FIG. 1 in an operator's hand.

FIG. 3 is a cross-sectional view of the device through lines 3-3 of FIG. 1.

FIG. 4 is a cross-sectional view of the device of FIG. 1-3 through lines 4-4 of FIG. 3.

FIG. 6 shows a speculum inserted into a vagina with a hysteroscope fed through the speculum into the uterus and the cervical occluding device within the speculum with the loop positioned around the exocervix.

DETAILED DESCRIPTION

Figure 5:
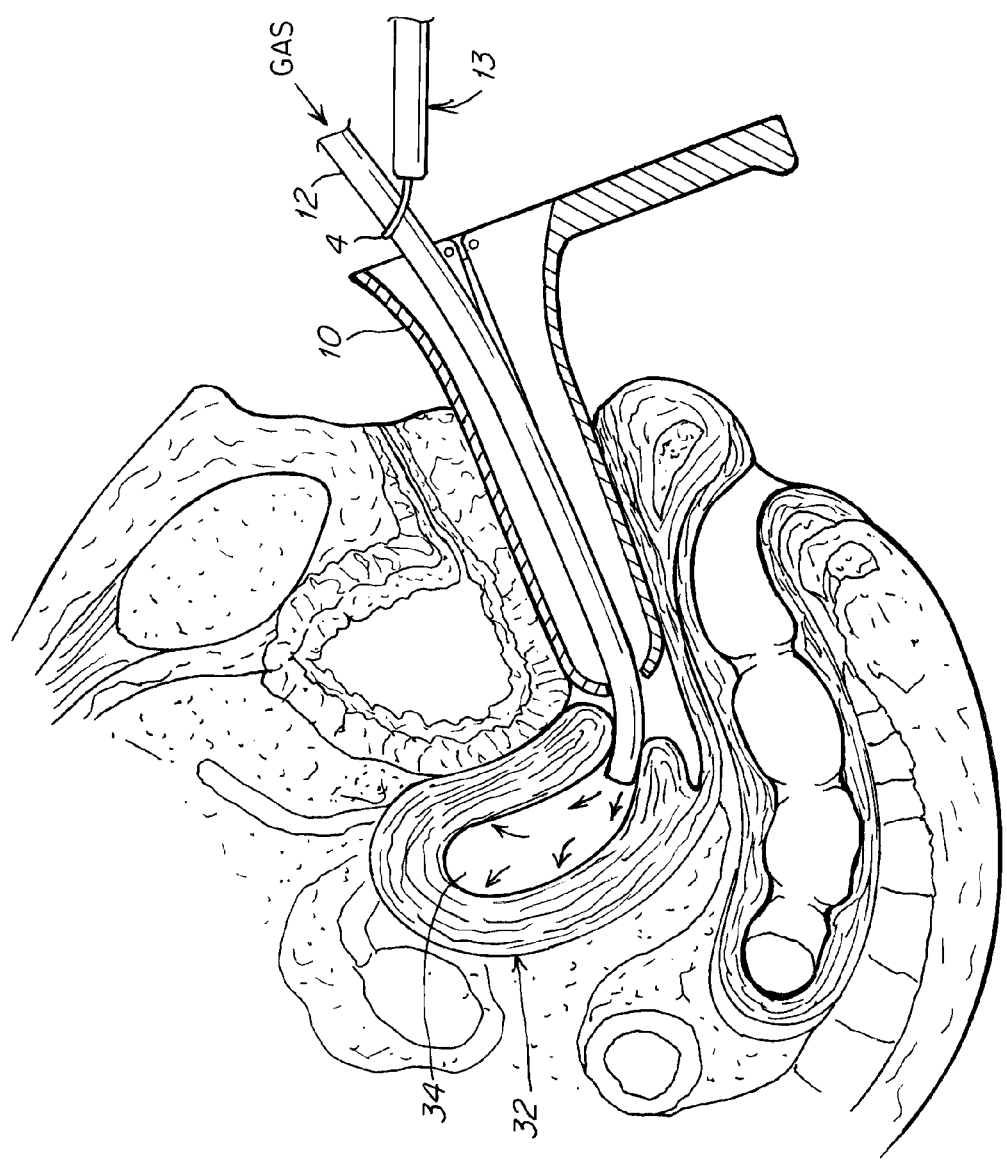
FIG. 5 shows a speculum inserted into a vagina with a hysteroscope fed through the loop of the cervical occluding device and through the speculum into the uterus.

This disclosure describes a device for occluding a cervix. As used herein, the term "cervix" includes the exocervix. As used herein, the term "about" means±10%.

As shown in the embodiment illustrated in FIG. 1, the device has an elongated conduit 1 sized and shaped to extend from proximal end 2 outside the vagina to distal end 3 near the cervix when inserted. Conduit 1 is held with a handle 7, which can be designed for left and right handed use, near proximal end 2. Generally, the conduit can range in length from about 4 inches (10 cm) to about 12 inches (30 cm). The conduit can have a uniform cross-sectional diameter, or as shown, can have multiple sections including a larger diameter section 1a and a smaller diameter section 1b. The conduit can include plastic or metal.

A loop 4 extends from distal end 3 of the conduit and is sized to fit around a patient's exocervix. Loop 4 is sufficiently flexible to be tightened and loosened around the exocervix. A portion of loop 4 is disposed inside conduit 1 and a portion of loop 4 protrudes from distal end of the conduit 3. The loop can include any suitable material that is flexible to fit around an exocervix and strong enough to tighten around the cervix, such as a synthetic material such as polypropylene, and can be formed as a mesh.

Referring to FIGS. 1 and 3, a rod 5 is provided inside conduit 1 and extends along much of the length of conduit 1. Rod 5 has a distal end and a proximal end, with loop 4 coupled to rod 5 at the distal end. Moving rod 5 longitudinally relative to conduit 1 tightens or loosens the loop. FIG. 1 shows the loop fully closed in solid lines and fully opened in dashed lines. The rod can include plastic or metal.

Rod 5 can be coupled to any suitable actuator for moving the rod, desirably an actuator that is manually movable without additional tools. Referring to FIGS. 1-4, one embodiment of such an actuator includes thumbslide 6 that has a tab 9 that protrudes through a slot opening in conduit 1 and allows the thumbslide and rod to be moved longitudinally.

Referring particularly to FIGS. 3 and 4, tab 9 for the thumbslide 6 extends through conduit 1 and into a molded piece 22 coupled to rod 5. Referring to FIG. 3, a pin 30 can be used as a connection between rod 5 and molded piece 22.

The device can include a lock for maintaining a position of the rod relative to the conduit to avoid one from moving longitudinally relative to the other after the loop has been positioned. Referring to FIG. 3, a series of teeth 24 can be disposed along the inside of an insert 23 to conduit 1. Molded piece 22 is coupled to a leaf spring 26 that catches on teeth 24 and holds the position of rod 5 relative to conduit 1 to avoid one from moving longitudinally relative to the other. Other suitable locks for maintaining a position of the rod relative to the conduit to avoid one from moving longitudinally relative to the other can also be used. For example, a threaded rod may extend through an opening in a knob coupled to the proximal end of the rod. A nut can be disposed on the threaded rod, where the nut can be tightened to prevent the rod from moving in a proximal direction. As another example, the slot for the slide can have a series of additional perpendicular slots so that the tab 9 is rotated slightly to fit into a slot to prevent the rod from moving longitudinally.

The resulting occlusion of the cervix by moving rod longitudinally in a proximal direction is reversible. By moving the rod in a distal direction, the loop may be loosened. After the loop is loosened, the loop may be removed from the cervix.

This disclosure also provides a method of occluding a cervix. In this method, a cervical occluding device as described above is inserted into a patient's vagina. Loop 4 is positioned around the patient's exocervix, and rod 5 is moved in a proximal direction, thereby tightening loop 4 around the exocervix. This tightening can be done before the uterus is distended. This method can further include inserting a hysteroscope or other instrument through the cervix before tightening the loop around the cervix.

Referring to FIGS. 5 and 6, the cervical occluder, the end of which is shown at 13, is useful during hysteroscopic procedures during which the uterine cavity is distended. During such procedures, a hysteroscope 12 can be introduced through the loop, a speculum 10, the cervix 32, and into uterine cavity 34. Once hysteroscope 12 is introduced to the uterine cavity, then the rod (FIGS. 1-4) can be moved longitudinally in a proximal direction to tighten loop 4 around cervix 32 and hysteroscope 12. The cervical occluder allows the uterine cavity to be distended and maintained without much discomfort to the patient and without injuring the cervix. Once the uterine cavity is distended, the clinician is able to proceed with the hysteroscopic procedure.

As shown in FIG. 6, cervical occluder 13 is fed through speculum 10 and into position proximate to cervix 32 so loop 4 (shown in dashed lines) is positioned around the exocervix. Once loop 4 is in position, cervix 32 can be occluded around hysteroscope 12 by operating the actuator in the occluder, such as by drawing back the thumbslide.

Loop 4 is removed by advancing the rod outwardly relative to the conduit (FIGS. 1-4). The loop should only require a small release of tension to allow it to be removed. The loop can be made from a material that has sufficient flexibility to close around the circumference of the exocervix, while also being sufficiently stiff to allow it to be released.

The cervical occluder can be provided as a multi-use product or a single-use disposable product. If multi-use, the design should allow for convenient cleaning and sterilization.

Other embodiments are within the scope of the following claims. For example, while certain materials have been described, others could be used.

The invention claimed is:

1. A device for occluding a cervix of a human through a vagina, comprising:
    an elongated straight conduit sized and shaped to extend from a proximal end outside the vagina to a distal end near the cervix;
    a loop sized to fit around an exocervix, the loop being sufficiently flexible to be tightened and loosened around the exocervix, wherein a portion of the loop is disposed inside the conduit and a portion of the loop protrudes from the distal end of the conduit;
    a hysteroscope that passes through the loop before the loop is tightened around the exocervix; and
    an actuator for causing the loop to be tightened and loosened around the exocervix.

2. The device of claim 1, further comprising a lock for maintaining a position of the actuator to inhibit the loop from tightening or loosening after the loop has been positioned.

3. The device of claim 2, wherein the lock includes teeth and a spring.

4. The device of claim 1, wherein the conduit further comprises a handle proximate to the proximal end.

5. The device of claim 1, wherein the actuator includes a rod disposed inside the conduit, the rod having a distal end and a proximal end, the loop joined to the distal end, and wherein moving the rod longitudinally relative to the conduit tightens or loosens the loop.

6. The device of claim 5, wherein the actuator further comprises a thumbslide coupled to the proximal end of the rod for moving the rod in a longitudinal direction.

7. The device of claim 1, wherein the loop includes synthetic mesh.

8. The device of claim 1, wherein the loop includes polypropylene.

9. The device of claim 1, wherein the device is a single use disposable device.

10. The device of claim 1, wherein the device consists essentially of the elongated straight conduit, the loop, and the actuator.

11. The device of claim 1, further comprising an opening in the conduit through which the actuator protrudes, wherein the conduit is a monolithic unit that has a smaller diameter at the distal end of the conduit than at the end with the opening.

12. A method comprising:
    inserting an occluding device into a patient's vagina, the occluding device comprising:
    an elongated straight conduit sized and shaped to extend from a proximal end outside the vagina to a distal end near the cervix;
    a loop sized to fit around an exocervix, the loop being sufficiently flexible to be tightened and loosened around the exocervix, wherein a portion of the loop is disposed inside the conduit and a portion of the loop protrudes from the distal end of the conduit; and
    an actuator for causing the loop to be tightened and loosened around the exocervix;
    positioning the loop of the occluding device around the patient's exocervix;
    inserting a hysteroscope into the patient's uterus through the patient's cervix and through the loop;
    and operating the actuator to tighten the loop around the exocervix.

13. A method comprising:
    inserting an occluding device into a patient's vagina, the occluding device comprising:
    an elongated conduit sized and shaped to extend from a proximal end outside the vagina to a distal end near the cervix;
    a loop sized to fit around an exocervix, the loop being sufficiently flexible to be tightened and loosened around the exocervix, wherein a portion of the loop is disposed inside the conduit and a portion of the loop protrudes from the distal end of the conduit; and
    an actuator for causing the loop to be tightened and loosened around the exocervix;
    positioning the loop of the occluding device around the patient's exocervix;
    operating the actuator to tighten the loop around the exocervix; and
    distending the patient's uterus cavity after the loop is tightened.

14. The method of claim 13, wherein the elongated conduit of the occluding device is straight.

15. A method comprising:
    inserting an occluding device into a patient's vagina, the occluding device comprising:
    an elongated conduit sized and shaped to extend from a proximal end outside the vagina to a distal end near the cervix;
    a loop sized to fit around an exocervix, the loop being sufficiently flexible to be tightened and loosened around the exocervix, wherein a portion of the loop is disposed inside the conduit and a portion of the loop protrudes from the distal end of the conduit; and
    an actuator for causing the loop to be tightened and loosened around the exocervix;
    inserting a hysteroscope into the patient's uterus through the patient's cervix;
    positioning the loop of the occluding device around the patient's exocervix; and
    operating the actuator to tighten the loop around the exocervix such that the hysteroscope remains extending into the uterus.

16. The method of claim 15, wherein the elongated conduit of the occluding device is straight.

17. The method of claim 15, further comprising inserting a speculum into the patient's vagina.

18. A method comprising:
    inserting a speculum into a patient's vagina;
    inserting an occluding device into the patient's vagina through the speculum, the occluding device comprising:
    an elongated conduit sized and shaped to extend from a proximal end outside the vagina to a distal end near the cervix;
    a loop sized to fit around an exocervix, the loop being sufficiently flexible to be tightened and loosened around the exocervix, wherein a portion of the loop is disposed inside the conduit and a portion of the loop protrudes from the distal end of the conduit; and
    an actuator for causing the loop to be tightened and loosened around the exocervix;
    positioning the loop of the occluding device around the patient's exocervix; and
    operating the actuator to tighten the loop around the exocervix.

19. the method of claim 18, wherein the elongated conduit of the occluding device is straight.

* * * * *